(12) United States Patent
Cho (10) Patent No.: US 11,266,314 B2
(45) Date of Patent: Mar. 8, 2022

(54) METHOD AND SYSTEM FOR DETERMINING A MATERIAL TYPE OF AN OBJECT OF INTEREST

(71) Applicant: ENDRA Life Sciences Inc., Ann Arbor, MI (US)

(72) Inventor: Jang Hwan Cho, Ann Arbor, MI (US)

(73) Assignee: ENDRA Life Sciences Inc., Ann Arbor, MI (US)

( * ) Notice: Subject to any disclaimer, the term of this patent is extended or adjusted under 35 U.S.C. 154(b) by 415 days.

(21) Appl. No.: 16/589,432

(22) Filed: Oct. 1, 2019

(65) Prior Publication Data

US 2021/0093202 A1 Apr. 1, 2021

(51) Int. Cl.
*A61B 5/00* (2006.01)
*G01N 29/24* (2006.01)
*A61B 5/05* (2021.01)
*A61B 8/00* (2006.01)
*G06T 7/00* (2017.01)

(52) U.S. Cl.
CPC ............ *A61B 5/0093* (2013.01); *A61B 5/05* (2013.01); *A61B 5/4872* (2013.01); *A61B 8/00* (2013.01); *G01N 29/2431* (2013.01); *G06T 7/0012* (2013.01)

(58) Field of Classification Search
CPC ....... A61B 5/0035; A61B 5/0093; A61B 5/05; A61B 5/4872; A61B 8/00; G01N 2291/044; G01N 22/00; G01N 25/20; G01N 29/0654; G01N 29/2431; G06T 7/0012
See application file for complete search history.

(56) References Cited

U.S. PATENT DOCUMENTS 9,888,879 B1 2/2018 Cho et al.
9,888,880 B1 2/2018 Cho et al.
9,980,677 B1 5/2018 Cho et al.

OTHER PUBLICATIONS

Lee Young; PCT International Search Report and Written Opinion; dated Dec. 31, 2020; 7 pages total; WIPO; Alexandria, VA, United States.

*Primary Examiner* — Amelie R Davis
(74) *Attorney, Agent, or Firm* — Stanley E. Jelic (57) ABSTRACT

A method for determining a material type of an object of interest comprises: directing, using a radio frequency (RF) source, RF energy into a region of interest, the region of interest comprising the object of interest, a known reference and a boundary between the object of interest and the known reference; detecting, using an acoustic receiver, at least one thermoacoustic multi-polar signal generated in response to the RF energy; correlating, by one or more processors, the at least one thermoacoustic multi-polar signal to a transmitted power correction factor to generate a corrected thermoacoustic multi-polar signal; and determining, by the one or more processors, the material type of the object of interest as a function of the corrected thermoacoustic multi-polar signal and a transmitted power of the RF energy.

20 Claims, 8 Drawing Sheets

METHOD AND SYSTEM FOR DETERMINING A MATERIAL TYPE OF AN OBJECT OF INTEREST

FIELD

The subject disclosure relates to thermoacoustic imaging and in particular, to a method and system for determining a material type of an object of interest.

BACKGROUND

Material types can be identified or quantified by making one or more measurements of the material and as a result, if the type of material is unknown, identification or quantification methods can be performed to identify the material type. These methods often require the use of specialized equipment. For example, dielectric measurement systems require a specialized probe and network analyzer.

In medical settings such as in a hospital, this specialized equipment may not be readily available. As will be appreciated, if required, it is desirable to determine one or more parameters of a material of interest using equipment that is readily available in a medical setting.

Although techniques for determining one or more parameters of a material have been considered, improvements are desired. It is therefore an object at least to provide a novel method and system for determining a material type of an object of interest.

SUMMARY

It should be appreciated that this summary is provided to introduce a selection of concepts in a simplified form that are further described below in the detailed description. This summary is not intended to be used to limit the scope of the claimed subject matter.

Accordingly, in one aspect there is provided a method for determining a material type of an object of interest, the method comprising: directing, using a radio frequency (RF) source, RF energy into a region of interest, the region of interest comprising the object of interest, a known reference and a boundary between the object of interest and the known reference; detecting, using an acoustic receiver, at least one thermoacoustic multi-polar signal generated in response to the RF energy; correlating, by one or more processors, the at least one thermoacoustic multi-polar signal to a transmitted power correction factor to generate a corrected thermoacoustic multi-polar signal; and determining, by the one or more processors, the material type of the object of interest as a function of the corrected thermoacoustic multi-polar signal and a transmitted power of the RF energy.

In one embodiment, directing, using a radio frequency (RF) source, RF energy into a region of interest, comprises using a thermoacoustic imaging system to direct RF energy pulses into the region of interest.

In one embodiment, detecting, using the acoustic receiver, at least one thermoacoustic multi-polar signal generated in response to the RF energy, comprises using one at least one thermoacoustic transducer array or at least one ultrasound transducer array to detect the at least one detecting, using an acoustic receiver, at least one thermoacoustic multi-polar signal generated in response to the RF energy.

In one embodiment the method comprises determining the transmitted power correction factor determined based on an input power of the RF source and an attenuation coefficient of the known reference.

In one embodiment, the method comprises determining the transmitted power correction factor based on an estimated thickness of the known reference and an attenuation coefficient of the known reference.

In one embodiment, each thermoacoustic multi-polar signal corresponds to a separate boundary location.

In one embodiment, the method further comprises: directing, using an ultrasound system, sound waves into the region of interest; detecting, using an ultrasonic transducer of the ultrasound system, echoes generated in the region of interest in response to the sound waves; processing ultrasound data associated with the echoes to generate one or more or more ultrasound images; and using the one or more ultrasound images to locate the region of interest.

In one embodiment, determining the material type of the object of interest is further based on at least one physical characteristic of the object of interest. The at least one physical characteristic may be at least one of color, transparency, odor, texture and material state.

In one embodiment, the object of interest is tissue within a human body and the known reference is lean tissue within the human body.

According to another aspect there is provided a system for determining a material type of an object of interest, the system comprising: a radio frequency (RF) source configured to direct RF energy toward the region of interest, wherein the region of interest comprises the object of interest, a known reference, and a boundary between the object of interest and the known reference; at least one thermoacoustic or ultrasonic transducer configured to receive a thermoacoustic multi-polar signal generated in response to the RF energy signal; and one or more processors configured to correlate the thermoacoustic multi-polar signal to a transmitted power correction factor to generate a corrected thermoacoustic multi-polar signal and to determine the material type of the object of interest as a function of the corrected thermoacoustic multi-polar signal and a transmitted power of the RF energy.

In one embodiment, the RF source is configured to direct RF energy pulses into the region of interest.

In one embodiment, the transmitted power correction factor is determined based on an input power of the RF source and an attenuation coefficient of the known reference.

In one embodiment, the transmitted power correction factor is determined based on an estimated thickness of the known reference and an attenuation coefficient of the known reference.

In one embodiment, each thermoacoustic multi-polar signal corresponds to a separate boundary location.

In one embodiment, the system further comprises an ultrasound imaging system configured to direct sound waves into the region of interest and detect echoes generated in the region of interest in response to the sound waves and wherein the one or more processors are configured to process ultrasound data associated with the echoes to generate one or more or more ultrasound images and use the one or more ultrasound images to locate the region of interest.

In one embodiment, the one or more processors are configured to determine the material type of the object of interest further based on at least one physical characteristic of the object of interest. The at least one physical characteristic may be at least one of color, transparency, odor, texture and material state.

In one embodiment, the known reference is one of a container and a pad.

According to another aspect there is provided a system for determining a material type of an object of interest, the system comprising: a thermoacoustic imaging system comprising a radio frequency (RF) applicator configured to emit RF energy pulses into the region of interest, the region of interest comprising an object of interest and a known reference separated by at least one boundary and an acoustic receiver configured to receive at least one thermoacoustic multi-polar signal induced in the region of interest in response to the RF energy pulses; and one or more processors configured to: correlate the at least one thermoacoustic multi-polar signal to a transmitted power correction factor to generate a corrected thermoacoustic multi-polar signal; and determine the material type of the object of interest as a function of the corrected thermoacoustic multi-polar signal and a transmitted power of the RF energy pulses.

BRIEF DESCRIPTION OF THE DRAWINGS

Embodiments will now be described more fully with reference to the accompanying drawings in which.

DETAILED DESCRIPTION OF THE EMBODIMENTS

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientation depicted in the figures.

In general, the subject disclosure discusses a method and system for identifying an unknown material based on thermoacoustic imaging, ultrasound imaging, and radio frequency properties.

For example, a thermoacoustic imaging system in conjunction with a known reference material or padding, can acquire a thermoacoustic signal for an unknown material. In this case, the known reference material or padding is placed on top of the unknown material and is used to characterize the properties of the unknown material. The unknown material requires a minimum amount of mass and minimum dimensions that correspond to the sensing limits of the thermoacoustic imaging system. When two materials are present, an unknown material and the known reference material or padding, during thermoacoustic imaging, thermoacoustic multi-polar signals occur at the boundary between the unknown material and known reference material or padding due to the different energy absorption rates of the unknown material and the known reference material or padding. Based on the phase and the strength of the thermoacoustic multi-polar signals, the thermoacoustic imaging system can identify a signature value of the unknown material. The signature value can comprise a Grüneisen parameter and a conductivity (or imaginary part of a permittivity).

Table I below shows examples of the Grüneisen parameter and conductivity of a number of materials. The Grüneisen parameter is dependent on the temperature of the material and usually has a linear relationship. The conductivity of the material depends on various factors such as the frequency and the temperature.

TABLE I

Examples of Grüneisen parameter and conductivity (at 434 MHz) of materials at room temperature

|  | Distilled water | Subcutaneous fat | Muscle | Blood | Mineral oil |
|---|---|---|---|---|---|
| Grüneisen parameter | 0.11 | 0.81 | 0.21 | 0.14 | 0.71 |
| Conductivity (S/m) | 0.045 | 0.042 | 0.80 | 1.36 | 0 |

An ultrasound imaging system can observe the speed of sound and scattering properties of imaged material and compare the scattering properties to a reference material. Ultrasound imaging can be accomplished with or without the known reference material or padding. Ultrasound imaging may be used to inspect the general material conditions and check for any undesirable structures that may interfere with thermoacoustic or radio frequency (RF) measurements, such as cracks or air bubbles.

With regard to radio frequency (RF) properties, such as the voltage standing wave ratio (VSWR), forward and reflected power, and impedance, these properties can be measured to check the impedance matching (or surface contact) between the measured material and the RF applicator. Such measurements can be obtained with and without the known reference material or padding.

Other potential observations (e.g., color, transparency, or other physical characteristics) of the unknown material can be compared to the reference material or padding. Table II summarizes properties of a number of materials that can be directly observed.

TABLE II

Example of other physical characteristics of materials

| | Distilled water | Fat | Mineral oil | Concrete |
|---|---|---|---|---|
| Color | Colorless | white | colorless | white/gray/colored |
| Transparency | Transparent | opaque | transparent | Opaque |
| Odor | Odorless | rancid | odorless | concrete odor |
| Texture | Smooth | smooth | smooth | Rough |
| material state | Liquid | solid | liquid | Solid |

Figure 1:
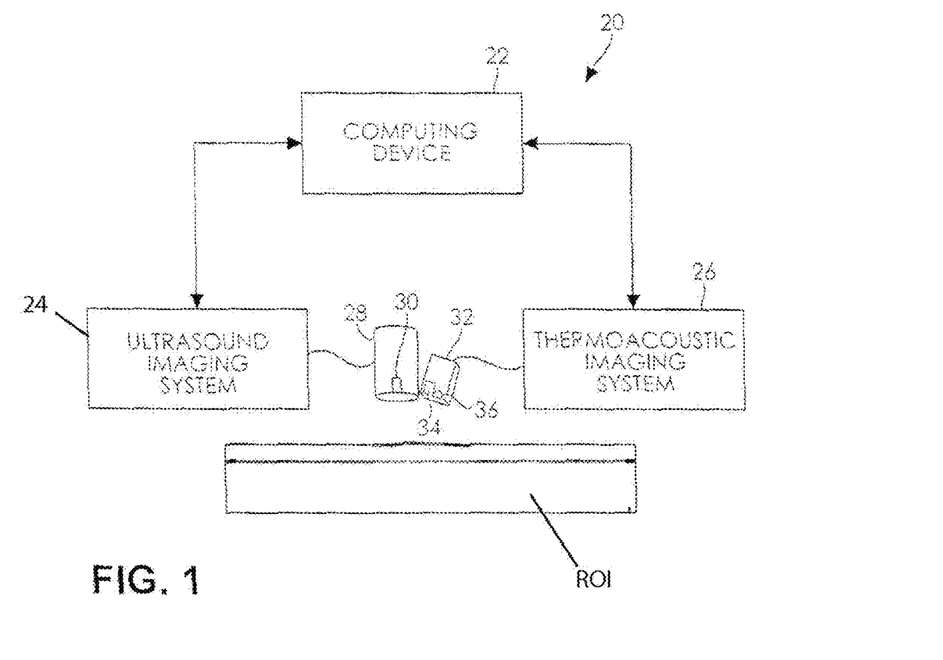
FIG. 1 is a schematic view of an imaging system wherein a region of interest is in vitro.

Turning now to FIG. 1, an exemplary imaging system is shown and is generally identified by reference numeral 20. As can be seen, the imaging system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a region of interest ROI.

The programmed computing device 22 in this embodiment is a personal computer, server or other suitable processing device comprising, for example, a processing unit comprising one or more processors, computer-readable system memory (volatile and/or non-volatile memory), other non-removable or removable computer-readable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, W-Fi, and/or other suitable network format, to enable connection to shared or remote drives, one or more networked computers, or other networked devices. One or more input devices, such as a mouse and a keyboard (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or the thermoacoustic image data received from thermoacoustic imaging system 26. The programmed computing device 22 executes program code stored on the computer-readable system memory and/or other non-removable or removable computer-readable memory and performs methods according to the program code as will be described further below.

The ultrasound imaging system 24 comprises an acoustic receiver in the form of an ultrasound transducer 28 that houses one or more ultrasound transducer arrays 30 configured to emit sound waves into the region of interest ROI. Sound waves directed into the region of interest ROI echo off materials within the region of interest ROI, with different materials reflecting varying degrees of sound. Echoes that are received by the one or more ultrasound transducer arrays 30 of the ultrasound transducer 28 are processed by the ultrasound imaging system 24 before being communicated as ultrasound image data to the computing device 22 for further processing and for presentation on the display device as ultrasound images that can be interpreted by an operator. In this embodiment, the ultrasound imaging system 24 utilizes B-mode ultrasound imaging techniques assuming a nominal speed of sound of 1,540 m/s. As ultrasound imaging systems are known in the art, further specifics of the ultrasound imaging system 24 will not be described further herein.

The thermoacoustic imaging system 26 comprises an acoustic receiver in the form of a thermoacoustic transducer 32. The thermoacoustic transducer 32 houses one or more thermoacoustic transducer arrays 34 as well as a radio frequency (RF) applicator 36. It will however be appreciated that the RF applicator 36 may be housed separately from the thermoacoustic transducer 32. The RF applicator 36 is configured to emit short pulses of RF energy that are directed into materials within the region of interest ROI. In this embodiment, the RF applicator 36 has a frequency between about 10 Mhz and 100 GHz and has a pulse duration between about 0.1 nanoseconds and 10 nanoseconds. RF energy pulses delivered to materials within the region of interest ROI induce acoustic pressure waves (thermoacoustic multi-polar signals) within the region of interest ROI that are detected by the thermoacoustic transducer 32. Acoustic pressure waves that are detected by the thermoacoustic transducer 32 are processed and communicated as thermoacoustic image data to the computing device 22 for further processing and for presentation on the display device as thermoacoustic images that can be interpreted by the operator.

In this embodiment, the ultrasound transducer 28 and thermoacoustic transducer 32 are mechanically interconnected so that the spatial relationship between the one or more ultrasound transducer arrays 30, the one or more thermoacoustic arrays 34 and the RF applicator 36 are known. The spatial relationship is set using a centerline of the one or more ultrasound transducer arrays 30, the one or more thermoacoustic transducer arrays 34, and RF applicator 36. The centerline of the ultrasound transducer array 34 and the thermoacoustic transducer array 34 is defined as being a mid-point of an area of the respective transduce array.

In this embodiment, the spatial relationship between the one or more ultrasound transducer arrays 30 and the one or more thermoacoustic transducer arrays 34 is such that the centerline of the one or more thermoacoustic transducer arrays 34 is set at a known angle $\alpha$ with respect to the centerline (also known as the axial axis or ultrasound transducer array beam axis) of the one or more ultrasound transducer arrays 30. The spatial relationship between the one or more thermoacoustic transducer arrays 34 and the RF applicator 36 is such that the centerline of the RF applicator 36 is spaced-apart and generally parallel to the centerline of the one or more thermoacoustic transducer arrays 34.

The imaging system 20 utilizes the known spatial relationship between the one or more ultrasound transducer arrays 30 and the one or more thermoacoustic transducer arrays 34 to increase the precision and accuracy of thermoacoustic imaging.

The coordinate system of the one or more ultrasound transducer arrays 30 of the ultrasound transducer 28 and the coordinate system of the one or more thermoacoustic transducer arrays 34 of the thermoacoustic transducer 32 are mapped by the computing device 22 so that acquired ultrasound and thermoacoustic images can be registered. Alternatively, the thermoacoustic imaging system 26 may make use of the one or more ultrasound transducer arrays 30 of the ultrasound transducer 28 by disconnecting the one or more ultrasound transducer arrays 30 from the ultrasound transducer 28 and connecting the one or more ultrasound transducer arrays 30 to the thermoacoustic transducer 32. As will be appreciated, by doing this coordinate mapping between the one or more ultrasound transducer arrays 28 and the one or more thermoacoustic transducer arrays 34 is not required.

Figure 2:
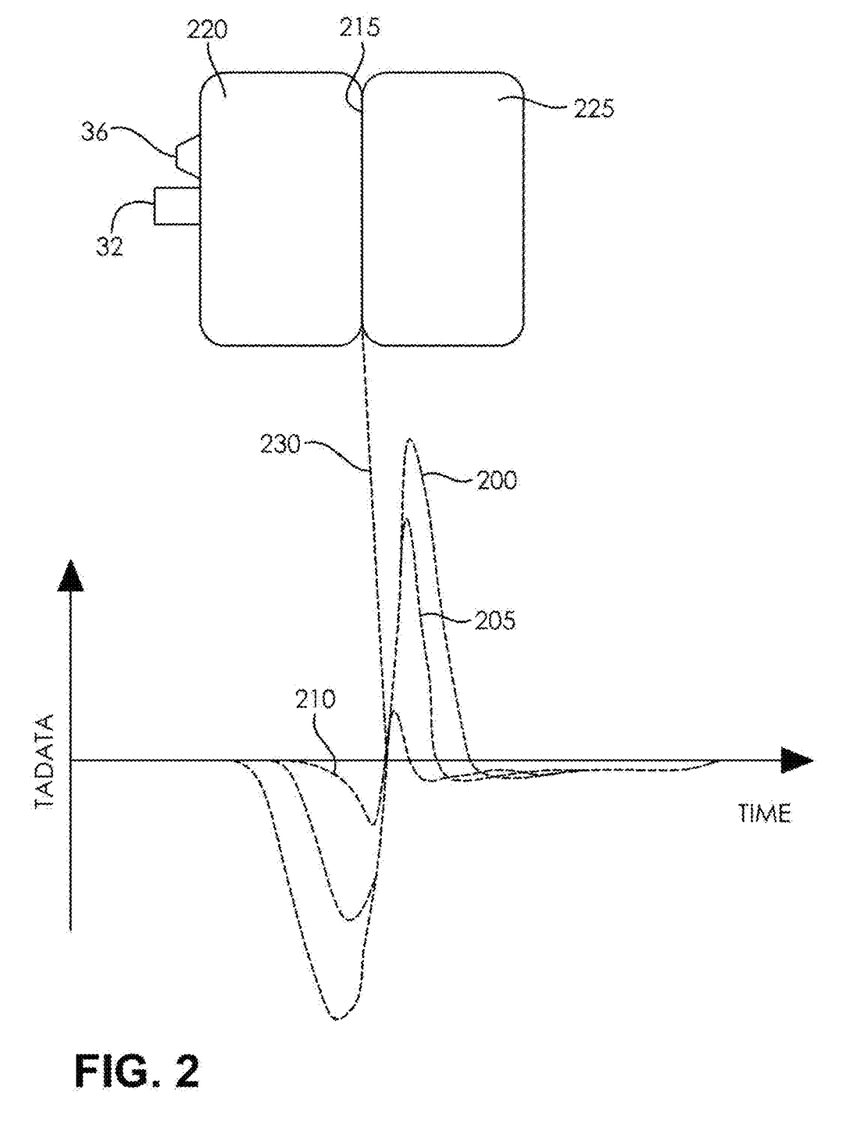
FIG. 2 is a graph showing exemplary thermoacoustic multi-polar signals generated in response to thermoacoustic imaging of a tissue region of interest comprising different tissue materials separated by a boundary.

Exemplary thermoacoustic multi-polar signals 200, 205 and 210 are shown in FIG. 2. The thermoacoustic multi-polar signals 200, 205 and 210 are generated in response to thermoacoustic imaging of a tissue region of interest ROI comprising a first tissue 220 and a different type of second tissue 225 that are separated by a boundary 215. The dashed line 230 indicates a time point corresponding to the boundary 215. The differences in the peak-to-peak values of the thermoacoustic multi-polar signals 200, 205 and 210 represent the extent to which the first tissue 220 expands into the boundary 215 and into the second material 225 in response to the delivered RF energy, before contracting. As the difference between the amount of RF energy absorbed by the two different tissues 220 and 225 at the boundary 215 increases, the amount that the first material 220 expands into the boundary 215 and into the second material 225 increases. Therefore, the peak-to-peak amplitude of each thermoacoustic multi-polar signal 200, 205 and 210 is proportional to the difference between the amount of RF energy absorbed by the two different tissues 220 and 225 at the boundary 215. As can be seen, the peak-to-peak value of thermoacoustic multi-polar signal 200 is greater than that of thermoacoustic multi-polar signals 205, 210 and the peak-to-peak value of thermoacoustic multi-polar signal 205 is greater than that of thermoacoustic multi-polar signal 210. As such, the difference between the amount of RF energy absorbed by the two different tissues 220 and 225 at the boundary 215 when thermoacoustic multi-polar signal 200 is generated, is greater than the difference between the amount of RF energy absorbed by the two different tissues 220 and 225 at the boundary 215 when thermoacoustic multi-polar signal 205 is generated. Similarly, the difference between the amount of RF energy absorbed by the two different tissues 220 and 225 at the boundary 215 when thermoacoustic multi-polar signal 205 is generated, is greater than the difference between the amount of RF energy absorbed by the two different tissues 220 and 225 at the boundary 215 when thermoacoustic multi-polar signal 210 is generated.

Figure 3:
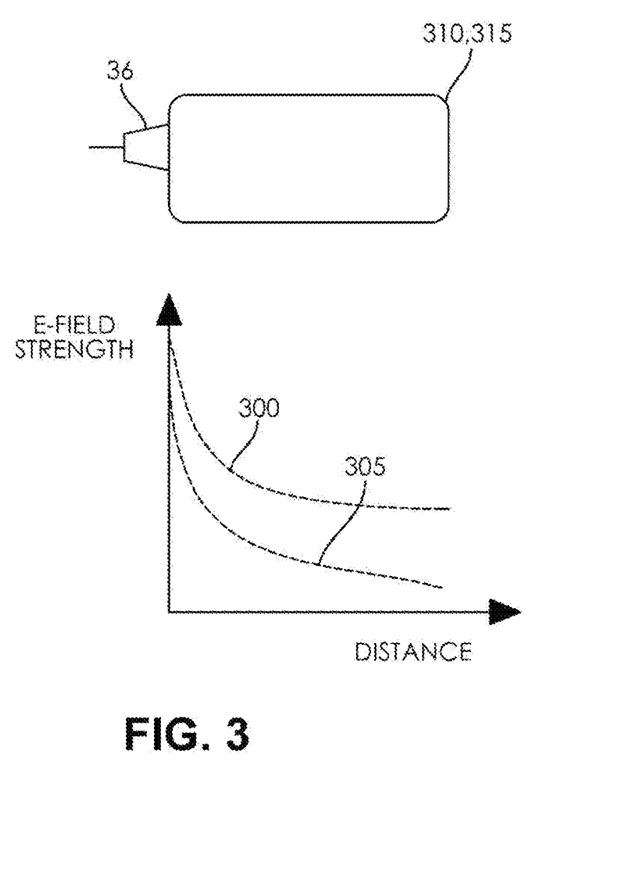
FIG. 3 is a graph showing exemplary electric field strength attenuation curves.

FIG. 3 shows electric field strength attenuation curves 300 and 305 in material 310 and 315 as a function of distance from the RF applicator 36. The example is simplified and ignores factors such as reflections off a boundary. Each electric field strength attenuation curve 300 and 305 represents the electric field strength attenuation of material 310, 315, respectively, as a function of distance from the RF applicator 36. The materials 310 and 315 have different attenuation coefficients (which could be the result of different fat concentrations in the respective materials). In this example, the material 310 associated with electric field strength attenuation curve 300 has a lower attenuation coefficient than the material 315 associated with electric field strength attenuation curve 305. The material 310 associated with electric field strength attenuation curve 300 has a high fat concentration (e.g. greater than 10%) and the material 315 associated with electric field strength attenuation curve 305 has a low fat concentration (e.g. less than 10%). The material 310 associated with electric field strength attenuation curve 300 also has a different Grüneisen parameter than the material 315 associated with electric field strength attenuation curve 305.

Figure 4:
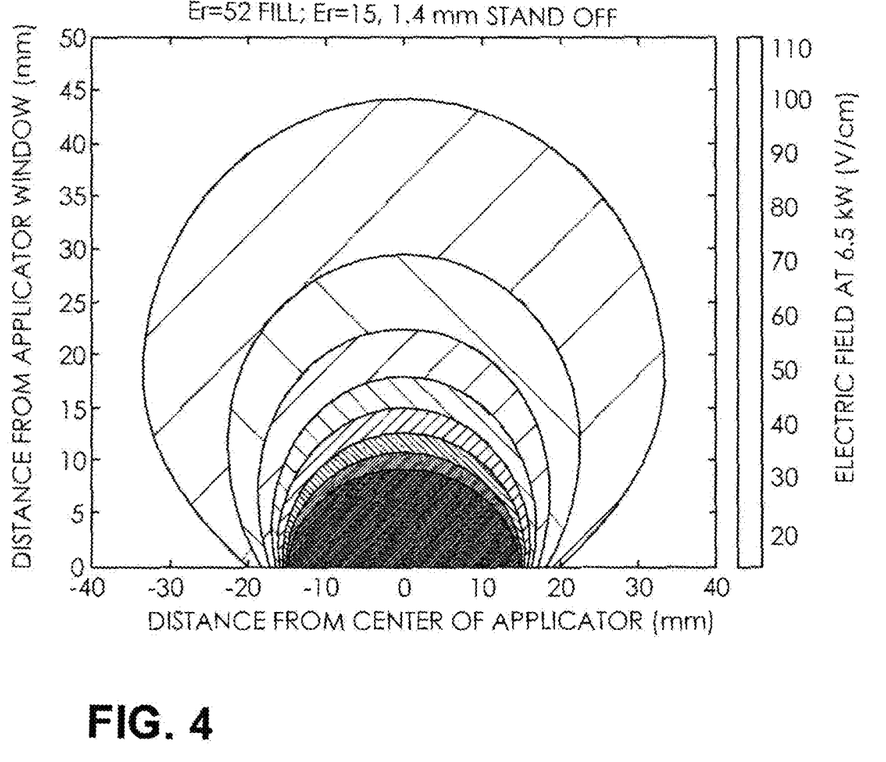
FIG. 4 is a graph showing exemplary flux (energy gradient) of radio frequency (RF) energy pulses.

FIG. 4 shows the flux (energy gradient) of an RF energy pulse generated by the RF applicator 36. The RF applicator 36 is located and centered at the 0 value of the x-axis. As can be seen, as the distance from the center of the RF applicator 36 increases, the electric field strength decreases.

Different materials have characteristic dielectric properties at a given frequency. The dielectric properties of a material determine how much energy is absorbed thereby. An electric field transmitted through the material is attenuated, and the amount of attenuation is determined by both dielectric and physical properties of the material. As an example, compared to lean tissue, fatty tissue absorbs less energy and thus attenuates less electric field. Knowing these properties, the amount of attenuation can be estimated. Furthermore, for a given RF applicator with specific design and tuning, dielectric properties of a material lead to different RF matching and energy delivery. For example, if the RF applicator 36 is tuned to match that of the human body, it is likely to match poorly to material with high water content, such as ultrasound gel. Therefore, knowing the RF power and matching properties provides information on the material in contact with the RF applicator 36.

Figure 5:
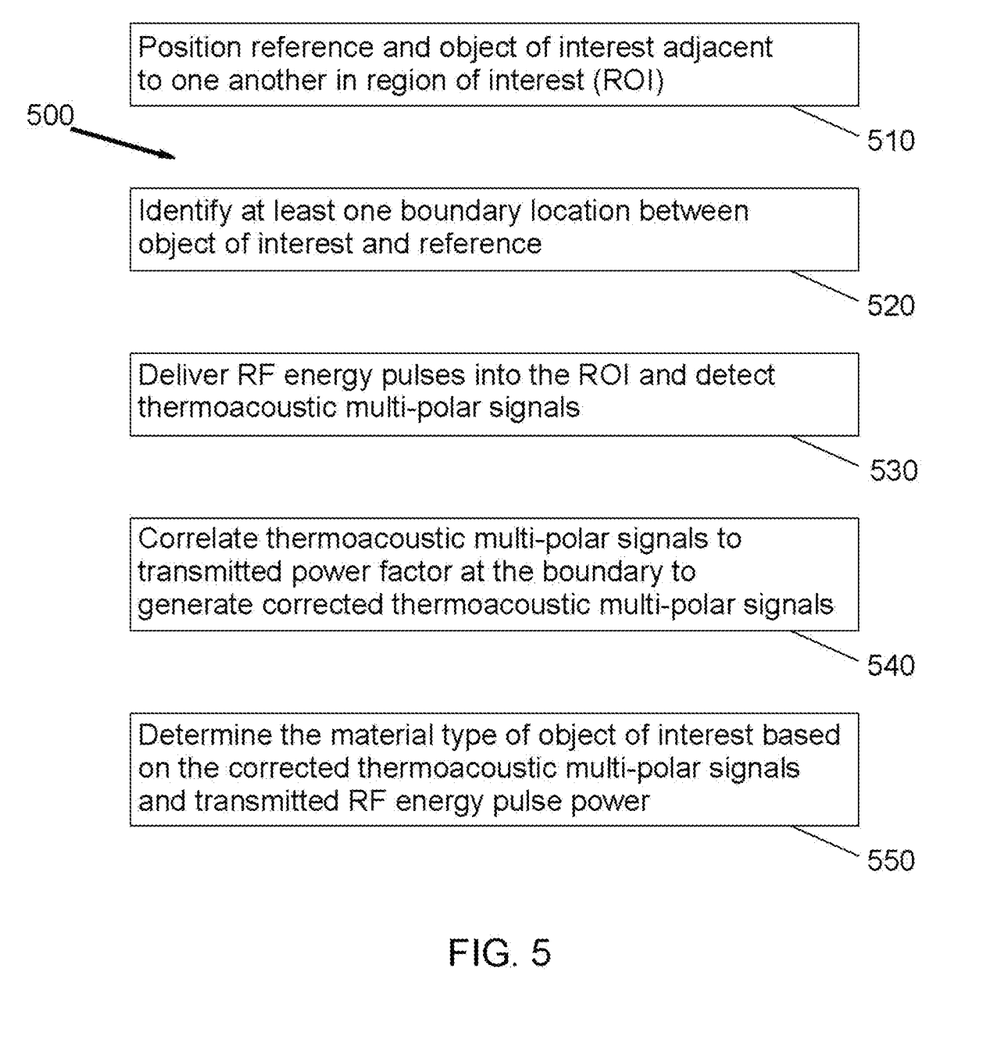
FIG. 5 is a flowchart of a method for determining a material type of an object of interest.
Figure 6:
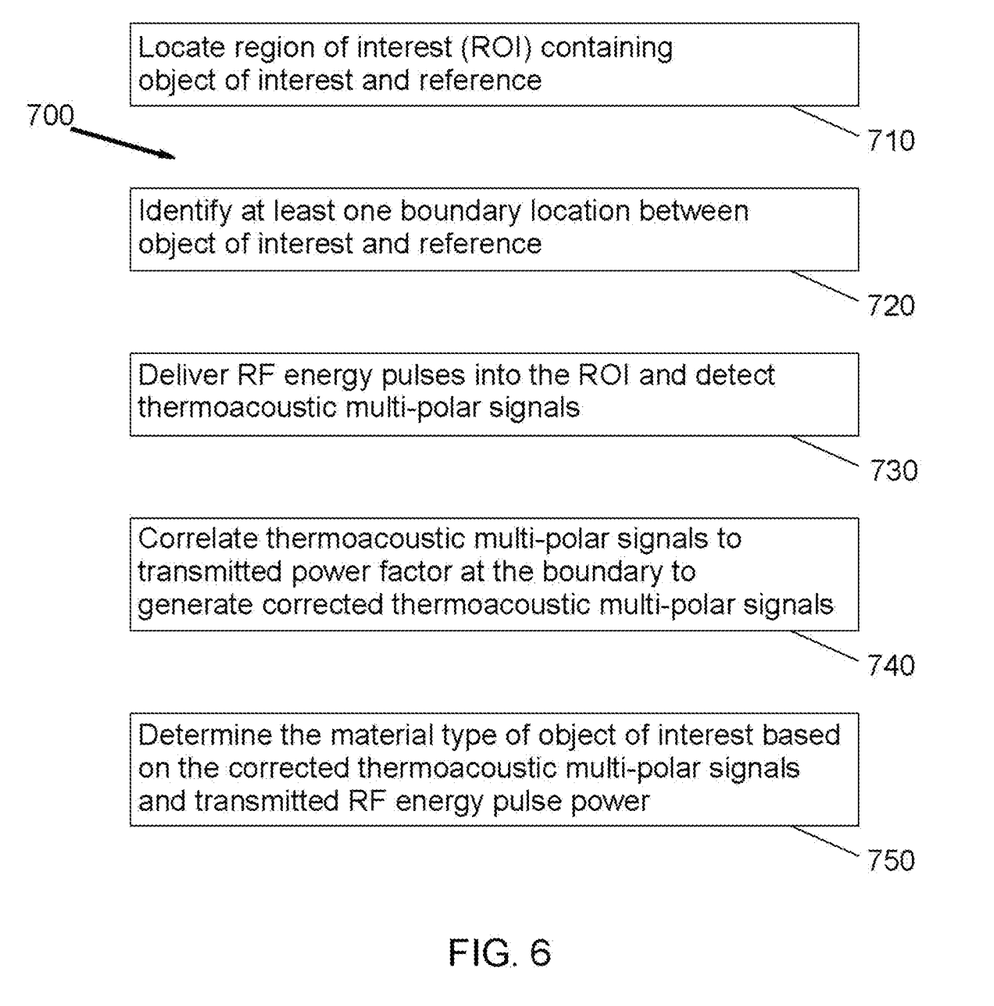
FIG. 6 is a flowchart of another method for determining a material type of an object of interest.

Turning now to FIG. 5, a method for determining a material type of an object of interest is shown and is generally identified by reference numeral 500. Initially during the method, a known reference and an object of interest are positioned adjacent to one another within the region of interest ROI (step 510). In an embodiment where the region of interest ROI is outside of a human body (i.e. in vitro), the known reference can be in the form of a pad that is made of a known material such as for example rubber. Other examples of pad construction can include but are not limited to gels made of materials such as agar, gelatin, gelwax, or the like. The pad should have known dielectric properties, low acoustic attenuation properties, minimal RF interference properties, and good acoustic matching properties. The known reference (e.g. pad) is placed over top of the object of interest.

The ultrasound imaging system 24 is used to image the region of interest ROI and at least one boundary location between the object of interest and the known reference is identified in the reconstructed ultrasound image (step 520). The thermoacoustic imaging system 26 is then used to image the region of interest ROI. As a result, RF energy pulses are delivered to the region of interest ROI. In response to the delivered RF energy pulses, at the boundary location, thermoacoustic multi-polar signals are generated that are detected and received by the thermoacoustic transducer 32 (step 530).

The thermoacoustic multi-polar signals received by thermoacoustic transducer 32 are communicated as thermoacoustic data to the computing device 22 for processing (step 540). In this embodiment, the computing device 22 is programmed to correlate the thermoacoustic multi-polar signals to a transmitted power correction factor to generate corrected thermoacoustic multi-polar signals. The computing device 22 is also programmed to determine the material type of the object of interest as a function of the corrected thermoacoustic multi-polar signals and a transmitted power of the RF energy pulses.

The thermoacoustic pressure p(r, t) produced by a heat source H(r, t) obeys the following equation:

$$\nabla^2 p(r, t) - \frac{1}{c^2} \frac{\partial^2}{\partial t^2} p(r, t) = -\frac{\beta}{C_p} \frac{\partial}{\partial t} H(r, t) \qquad (1)$$

where r is the spatial position vector, β is the isobaric volume expansion coefficient, c is the sound speed and $C_p$ is the specific heat capacity. Solving equation 1 with respect to the acoustic pressure wave p(r, t) yields the following forward problem:

$$p(r, t) = \frac{\beta}{4\pi C_p} \int\int\int \frac{\partial r}{|r - r'|} \frac{\partial H(r', t')}{\partial t'} \bigg|_{t' = t - \frac{r'}{c}} \qquad (2)$$

The heat source H(r, t) is modeled as the product of two factors, which are the spatial distribution of energy absorption A(r) and the temporal irradiation function I(t). The spatial distribution of energy absorption A(r) is determined based on characteristics of the material(s) being imaged. Since the thermoacoustic transducer array 30 has a finite bandwidth, received thermoacoustic data $p_d$(r, t) is a result of the convolution of acoustic pressure wave p(r, t) and the impulse response of the thermoacoustic transducer array 30 h(t) as set out in equation 3:

$$p_d(r,t) = p(r,t) *_t h(t) \qquad (3)$$

where $*_t$ denotes a one-dimensional temporal convolution.

As will be appreciated, for conventional thermoacoustic imaging, the goal is to recover the spatial absorption distribution A(r) by inverting the forward problem. As such, the irradiation function is modeled as a temporal function that is uniform at a given time point.

Due to the limited bandwidth of the thermoacoustic transducer array 30, accurately recovering the absorption distribution is not trivial. As such, extracting quantitative information requires sophisticated methods beyond that of conventional reconstruction methods.

When the object of interest is heated with a pulse of RF energy, the power deposition per unit volume A(r) is expressed as:

$$A(r) = \omega \varepsilon_0 \varepsilon''_r E^2(r) \qquad (4)$$

where ω is the radian frequency, $\varepsilon_0$ is the vacuum permittivity, $\varepsilon''_r$ is the imaginary part of the relative permittivity (also referred to as the conductivity) of the material of interest and E(r) is the electric field strength. The strength of thermoacoustic data S(r) obtained from the object of interest is the product of the deposited energy and the Grüneisen parameter of the tissue Γ:

$$S(r) = \Gamma A(r) = \Gamma \omega \varepsilon_0 \varepsilon''_r E^2(r) \qquad (5)$$

Within a dielectric lossy medium, the electric field strength is attenuated as it propagates through the medium. The amount of attenuation is determined by various factors such as for example characteristics of object of interest and characteristics of the RF applicator 36. The spatial distribution of the electric field can be expressed as:

$$E(r) = E_0 E_A(r) \qquad (6)$$

where $E_0$ is the maximum electric field strength of the region of interest and $E_A$(r) is the attenuation of the electric field over a given space. For a simple one-dimensional case, the attenuation $E_A$(r) can be expressed in exponential form:

$$E_A(d) = e^{-\eta d} \qquad (7)$$

where η is the electric field absorption coefficient of the region of interest and d is the distance of the region of interest ROI from the RF applicator 36.

In this embodiment, equation 5 is used as a model to infer object material parameters from the thermoacoustic data. As mentioned, thermoacoustic data obtained from the region of interest ROI is in the form of thermoacoustic multi-polar signals. The strength or peak-to-peak amplitudes of the thermoacoustic multi-polar signals represent the absorption property difference between the object of interest and the known reference. Further, the phase of the thermoacoustic data at the boundary indicates which material (the material of the object of interest or the known reference) has a higher or lower absorption coefficient. The strength or peak-to-peak amplitudes $S_l$ of each thermoacoustic multi-polar signal measured at the boundary location, r, is expressed in equation 8:

$$S_l = (\Gamma_{MOI} \varepsilon''_{r,MOI} - \Gamma_{ref} \varepsilon''_{r,ref}) \omega \varepsilon_0 E_l^2 \qquad (8)$$

where MOI denotes the material of the object of interest, ref denotes the known reference, and $E_l$ denotes the incident electric field strength at the boundary.

As shown in equation 8, the strength of each thermoacoustic multi-polar signal is determined by material parameters and the strength of the electric field at the boundary.

Since the properties of the reference are known, to estimate the properties of the material of the object of interest, only the strength of the electric field at the boundary is required. Put another way, since the material of the object of interest has different dielectric and/or thermoacoustic properties than the known reference, the properties of the material of the object of interest can be deduced.

Using equation 6, the incident electric field $E_l$ at the boundary location (going from the known reference to the object of interest) can be estimated as:

$$E_l = E_0 e^{-n_{ref} d_{ref}} \qquad (9)$$

where $E_0$ is the electric field strength at the start of the known reference, $n_{ref}$ is the attenuation coefficient of the known reference, and $d_{ref}$ is a thickness of the known reference. As will be appreciated, the electric field strength $E_0$ may be modeled using a finite-difference time domain (FDTD) method or may be inferred from measurements taken at the RF applicator 36. The electric field strength $E_0$ may alternatively be directly measured at the boundary using an electric field probe.

The thermoacoustic multi-polar signal strength at the boundary location can be derived from equations 8 and 9 as:

$$S_l = (\Gamma_{MOI} \varepsilon''_{r,MOI} - \Gamma_{ref} \varepsilon''_{r,ref}) \omega \varepsilon_0 E_l^2 \qquad (10)$$

$$= (\Gamma_{MOI} \varepsilon''_{r,MOI} - \Gamma_{ref} \varepsilon''_{r,ref}) \omega \varepsilon_0 \left(E_0 e^{-n_{ref} d_{ref}}\right)^2$$

Parameter $k_{MOI}$ of the object of interest can be calculated as:

$$k_{MOI} = \Gamma_{MOI} \varepsilon''_{r,MOI} = \frac{S_l}{\omega \varepsilon_0 \left(E_0 e^{-n_{ref} d_{ref}}\right)^2} + \Gamma_{ref} \varepsilon_0 \varepsilon''_{r,ref} \qquad (11)$$

Calculating the parameter $k_{MOI}$ requires accurate modeling of the electric field based on attenuation property of the known reference material. Instead, the estimation can be done based on a lookup table created from synthetic objects or phantoms with various known properties. By using known synthetic objects, the need for such accurate modeling can be bypassed. However, having accurate electric field modeling will still have benefits since the electric field distribution will change depending on the object of interest being scanned.

Creating the lookup table requires thermoacoustic imaging of each known synthetic object in conjunction with the known reference. During thermoacoustic imaging of a known synthetic object and known reference, at the boundary of the known reference and the known synthetic object with certain property, the thermoacoustic multi-polar signal strength will be:

$$S_{syn} = (\Gamma_{syn}\varepsilon''_{r,syn} - \Gamma_{ref}\varepsilon''_{r,ref})\omega\varepsilon_0 E_I^2 \quad (12)$$

$$= (\Gamma_{syn}\varepsilon''_{r,syn} - \Gamma_{ref}\varepsilon''_{r,ref})\omega\varepsilon_0 E_0^2 e^{-2\eta_{ref}d_{ref}}$$

From equations (10) and (11), the following expression can be obtained:

$$\frac{S_{obj}}{S_{syn}} = a(\Gamma_{obj}\varepsilon''_{r,obj} - \Gamma_{ref}\varepsilon''_{r,ref})/(\Gamma_{syn}\varepsilon''_{r,syn} - \Gamma_{ref}\varepsilon''_{r,ref}) \quad (13)$$

where $\alpha$ is a scaling factor correcting for transmitted power differences between the synthetic object or phantom and the object of interest. Rearranging the terms of equation 13 results in equation 14 below:

$$\kappa_{obj} \equiv \Gamma_{obj}\varepsilon''_{r,obj} = \Gamma_{ref}\varepsilon''_{r,ref} + \left(\frac{1}{a}\right)\left(\frac{S_{obj}}{S_{syn}}\right)(\Gamma_{syn}\varepsilon''_{r,syn} - \Gamma_{ref}\varepsilon''_{r,ref}) \quad (14)$$

For different synthetic objects or phantoms and objects of interest, the parameter $\kappa_{obj}$ can be tabulated from models and experiments to generate $\kappa_{obj,syn}$. Each component of $\kappa_{obj}$ can be either measured or modeled for each synthetic object or phantom and each object of interest. The parameter $\kappa_{obj}$ will be a unique value for each object of interest and a given synthetic object or phantom. If there are multiple synthetic objects or phantoms, then there would be multiple K values for a single object of interest. In one embodiment, the parameter $\kappa_{obj,syn}$ would be utilized instead of $\kappa_{obj}$ since the products of unknown quantities of the unknown material type depend upon the object of interest and the synthetic object or phantom used.

$\kappa_{obj,syn}$ can be considered as a function depending on both object and synthetic object. For a given synthetic object (syn1), we'll get $\kappa_{obj,syn1}$. For another (syn2), we'll get $\kappa_{obj,syn2}$.

The synthetic objects or phantoms can be made from various liquids and solids including, but not limited to, water, gel, wax, agar, TX-151, TiO2, or some combination thereof. The synthetic objects or phantoms, can have wide ranges of dielectric properties and Grüneisen parameters. In this embodiment, the synthetic objects or phantoms and the known reference are scanned and their thermoacoustic measurements and power measurements are recorded. The recorded measurements and metrics calculated from the measurements are tabulated into a multi-dimensional lookup table. For the lookup table, the thermoacoustic multi-polar signal strength is normalized by the forward power to compensate for power variations between synthetic objects or phantoms. In one embodiment, the real relative part of the permittivity is between 5 and 100 (dimensionless).

In a separate embodiment, a single synthetic object or phantom is used to generate a multi-dimensional lookup table instead of multiple synthetic objects or phantoms. To generate the lookup table data with a single synthetic object or phantom, a scaling factor correcting for forward power differences between the synthetic object or phantom and object of interest is used. Comparing the set of measured parameters to known parameters enables a user to determine the material type of the object of interest based upon the closest match to known parameters.

Various measurements from given thermoacoustic data can be used to construct a metric, which can be also be tabulated and used to identify the material type of the object of interest. For example, thermoacoustic measurements may have no object related response signals at the beginning of the measurements. Such no object related response signals may come from the coupling medium (e.g. ultrasound gel), from internal components or transducer components, the boundary between the known reference and the RF applicator 36, from internal components of the RF applicator 36, etc. Response signals from such sources are independent of the object of interest and can be used to compensate or normalize the thermoacoustic multi-polar signals from the object of interest. The simple ratio between the thermoacoustic multi-polar signals at the boundary between the known reference and the object of interest and a material independent response signal can be used as a metric. If there are multiple material independent response signals, other metrics can be constructed from various combinations of them.

Those skilled in the art will appreciate that the ultrasound imaging system may be used to help identify the material of interest. For example, the speed of sound and scattering properties of the material of interest can be observed and compared to the speed of sound and scattering properties of the reference. The ultrasound imaging system may also be used to inspect a condition of the material of interest and to check for undesirable structures such as for example cracks or air bubbles that may interfere with the thermoacoustic imaging process.

Those skilled in the art will appreciate that radio frequency (RF) characteristics may be used to help identify the material of interest. For example, the RF forward and reflected power of the RF energy pulses may be monitored. As is known, the RF forward power is the power of the RF energy pulses emitted by the RF applicator. The RF reflected power is the power of the RF energy pulses that are reflected back to the RF applicator. Using the RF forward and reflected powers, the voltage standing wave ratio (VSWR) can be calculated and is a measure of how efficiently RF power is being transmitted from the RF applicator.

In this embodiment, RF energy pulses are directed through at least one intermediate area and into a region of interest that comprises the material of interest. The RF energy pulses have a known frequency and a known amplitude. A first power monitor is used to measure the forward power of the RF energy pulses. A second power monitor is used to measure the reflected power of the RF energy pulses. The RF forward and reflected powers may be acquired with or without the reference present.

In this embodiment, the VSWR is calculated as a ratio of the measured forward power and the measured reflected power. Using the measured forward power, the VSWR, and an estimated thickness of the at least one intermediate area, a parameter of the material of interest may be estimated using a lookup table.

Those skilled in the art will appreciate that the phase of the thermoacoustic multi-polar signals may be used to help identify the material of interest. Since the reference is made of a known material, the material (the material of interest or the reference) that absorbs more heat than the other material expands rapidly across the boundary and into the other material, that expands less, and then quickly contract. The phase of the bipolar acoustic signal depends on which one of the materials absorbs more heat.

Those skilled in the art will appreciate that the strength or peak-to-peak values of the multi-polar acoustic signals may be used to help identify the material of interest. Since the reference is made of a known material with a known absorption property and the strength or peak-to-peak values of the multi-polar acoustic signals depend on the relative absorption properties of the materials, the absorption property of the material of interest can be deduced.

Although the system is designed such that the boundary between the known reference and the unknown material of the object of interest is close to parallel to the surface of the transducer array, the shape of the boundary may be deformed depending on the object of interest. In such cases, the acquired thermoacoustic measurements need to be compensated for such deformation. The amount of deformation can be estimated based on the ultrasound imaging and/or acquired thermoacoustic measurements. For one skilled in the art, estimating the shape and the angle of the boundary from ultrasound image is well established. Deformation can also be estimated using thermoacoustic measurements based on the angle in the two-dimensional measurement domain and also on the shape of the thermoacoustic multi-polar signals.

Received signals at the thermoacoustic transducer array 34 may be expressed using equation 15:

$$p_S(t) = \int_S p(\underline{r},t)dS \quad (15)$$

where S is the surface area of the thermoacoustic transducer array. As will be appreciated, the properties of the thermoacoustic transducer array and its positioning relative to the object of interest change the characteristics of the thermoacoustic data. The thermoacoustic multi-polar signals received by the thermoacoustic transducer array are affected by various factors that are not related to signal generation by rather associated with signal propagation. These factors depend on transducer spatial sensitivity, relative positioning between the thermoacoustic transducer array and the boundary between the object of interest and the known reference, and the relative shape of the known reference with respect to the thermoacoustic transducer array surface. Even for the same region of interest and the same thermoacoustic transducer array, changing the position and angle of the thermoacoustic transducer array during thermoacoustic data acquisition results in different measurements.

In this embodiment, a compensation factor is calculated based on information and measurements provided by the operator or estimated using acquired ultrasound image data. The compensation factor may be a single factor or multiple factors, where each factor is calculated information such as size and shape of the known reference and the angle between the ultrasound transducer array and the boundary. In one embodiment, the compensation factors are calculated based on theoretical methods such as by using acoustic propagation and ultrasound transducer properties. In another embodiment, the compensation factors may be obtained from phantoms and clinical studies. In yet another embodiment, both theoretical and experimental methods may be used.

When the thermoacoustic data is adjusted with the compensator factor, the thermoacoustic signal strength, $S_I$, in equation 11 is replaced by the adjusted thermoacoustic signal strength, $\underline{S}_I$:

$$\kappa_{obj} \equiv \Gamma_{obj}\varepsilon''_{r,obj} = \Gamma_{ref}\varepsilon''_{r,ref} + \left(\frac{1}{a}\right)\left(\frac{\overline{S}_{obj}}{\overline{S}_{syn}}\right)(\Gamma_{syn}\varepsilon''_{r,syn} - \Gamma_{ref}\varepsilon''_{r,ref}) \quad (16)$$

When the object of interest is large enough to ignore the partial volume effect, only the angle based adjustment is required. When a tangent vector of the object of interest at the boundary and the centerline of the one or more transducer arrays 34 is not perpendicular, signal adjustment is made to the acquired measurement. This adjustment is expressed as:

$$\underline{S}_I = S_I C(\theta) \quad (17)$$

where C is an angle based adjustment factor, $\theta$ is the angle between the tangent vector of the object of interest at the boundary and the centerline of the one or more transducer arrays 34.

Table III below is an example lookup table which determines material type as a function of a corrected thermoacoustic multipolar signal at the boundary, a forward power of the energy signal, and a voltage standing wave ratio of the energy signal.

TABLE III

Example of lookup table

| Measurements | | | Material 1 | Material 2 |
|---|---|---|---|---|
| Quantitative | Thermoacoustic | Material independent characteristic TA signal Corrected TA signal at the reference to material boundary Characteristic TA property against synthetic object #1 (phantom #1) (Grüneisen × Conductivity) Characteristic TA property against synthetic object #2 (phantom #2) (Grüneisen × Conductivity) | | |

TABLE III-continued

Example of lookup table

| Measurements | | | Material 1 | Material 2 |
|---|---|---|---|---|
| | Power measurements (no reference) | Forward | | |
| | | Transmitted | | |
| | | VSWR | | |
| | Power measurements (with reference) | Forward | | |
| | | Transmitted | | |
| | | VSWR | | |
| | Combined metrics | Ratio between TA signals | | |
| | | Function of ratio between TA signals and TA properties | | |
| | | Function of TA signal, properties, and power measurements | | |
| | Ultrasound | Speed of sound | | |
| Semi-quantitative | Ultrasound | Scattering | | |
| Other characteristics | Color | | | |
| | Transparency | | | |
| | Texture | | | |
| | Material state | | | |
| | Odor | | | |

Semi-quantitative measurements may be used to help identify the material of interest. For example, for a material with an unknown condition, each quantitative property may be compared against conditions listed in Table Ill. An exemplary comparison metric is shown in equation 18:

$$Q_i = \Sigma_{j=1}^{N}(p^j_i - p^j_{unknown})w^j \quad (18)$$

where N is the total number of quantitative property being included in the comparison, i denotes the $i^{th}$ condition in the lookup table, j denotes $j^{th}$ material property, $p^j_i$ denotes the $j^{th}$ property of material with $i^{th}$ condition $p^j_{unknown}$ denotes the $j^{th}$ property of the material with unknown condition, $w^j$ denotes a weighting factor for $j^{th}$ property. Material with the lowest $Q_i$ will be considered as the identified condition of the material. As will be appreciated, only part of the materials properties may be used to determine the material condition.

In some embodiments, the identity of the material will not be directly selected from the lookup table, but the likelihood of its identity will be suggested based on the acquired metrics. For example, a material may have 60% likelihood to be material 1 and 40% likelihood to be material 2.

In some embodiments, the identity of material will be proposed as a weighted combination of multiple materials, based on the acquired metrics.

In some embodiments, the parameter or the condition of the material of interest will be proposed as a weighted combination of multiple materials, based on the acquired metrics.

In some embodiments, various measurements from thermoacoustic data can be used to construct a parameter, which may be tabulated and used to help identify the material. For example, thermoacoustic data having no object related signals may be obtained at the beginning of the measurements. For example, thermoacoustic data may be obtained with the coupling medium (e.g., ultrasound gel) being present, thermoacoustic data may be obtained and may comprise signals generated from internal components or transducer components, the boundary between the reference and the RF applicator, the internal components of the RF applicator, or other parts of the RF applicator. Thermoacoustic data from such sources are independent of the material and can be used to compensate or normalize the thermoacoustic signal from the material. A simple ratio between thermoacoustic data obtained at the reference to the boundary and thermoacoustic data having no object related signals may be used as a metric. As will be appreciated, various combinations of thermoacoustic data having no object related signals may be obtained.

Those skilled in the art will appreciate that in embodiments, the boundary between the reference and the material of interest may be automatically defined using algorithms based on ultrasound segmentation or thermoacoustic data analysis. As will be appreciated, both operator-defined and automatic methods may be combined.

Although the reference is described as being in the form of a pad made of a known material and is placed on top of the object of interest, those skilled in the art will appreciate that alternatives are available. For example, in another embodiment the known reference may be in the form of a container or petri dish configured to hold or contain the object of interest.

Figure 7:
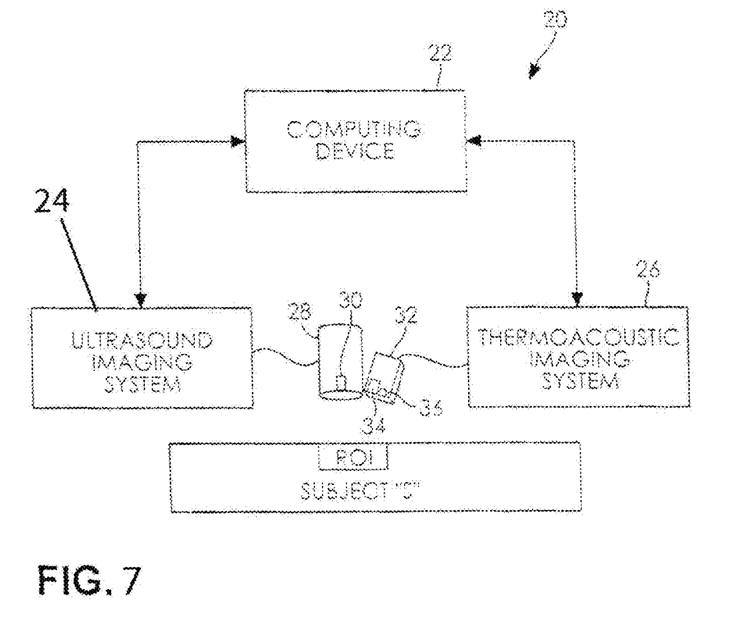
FIG. 7 is a schematic view of the imaging system wherein the region of interest is in vivo.

Turning now to FIG. 7, another embodiment of a method for determining the material type of an object of interest is shown and is generally identified by reference numeral 700. Method 700 is generally identical to that of method 500 with the following exceptions. During method 700, rather than the region of interest being in vitro, in method 700 region of interest is in vivo. As such, initially during the method, a region of interest ROI to be imaged that contains the object of interest and a reference separated by at least one boundary is located within a subject's body (step 510). In this embodiment, the region of interest ROI is located using the ultrasound imaging system 24. Specifically, ultrasound image data obtained by the ultrasound imaging system 24 is communicated to the computing device 22. The ultrasound image data is processed by the computing device 22 and a reconstructed ultrasound image is presented on the display device. The operator moves the ultrasound transducer 28 until the region of interest is located. When locating the region of interest, the computing device 22 overlays information associated with the angle of the centerline of the one or more transducer arrays 30 of the ultrasound transducer 28 over top of the reconstructed ultrasound image on the display device. The information is used to provide feedback to the operator to ensure the axial axis of the ultrasound transducer 28 is generally perpendicular to a boundary between the object of interest and the reference.

Once the region of interest ROI has been located, steps 720, 730, 740 and 750 of method 700 are generally identical to that of steps 520, 530, 540 and 550 of method 500, respectively.

Figure 8:
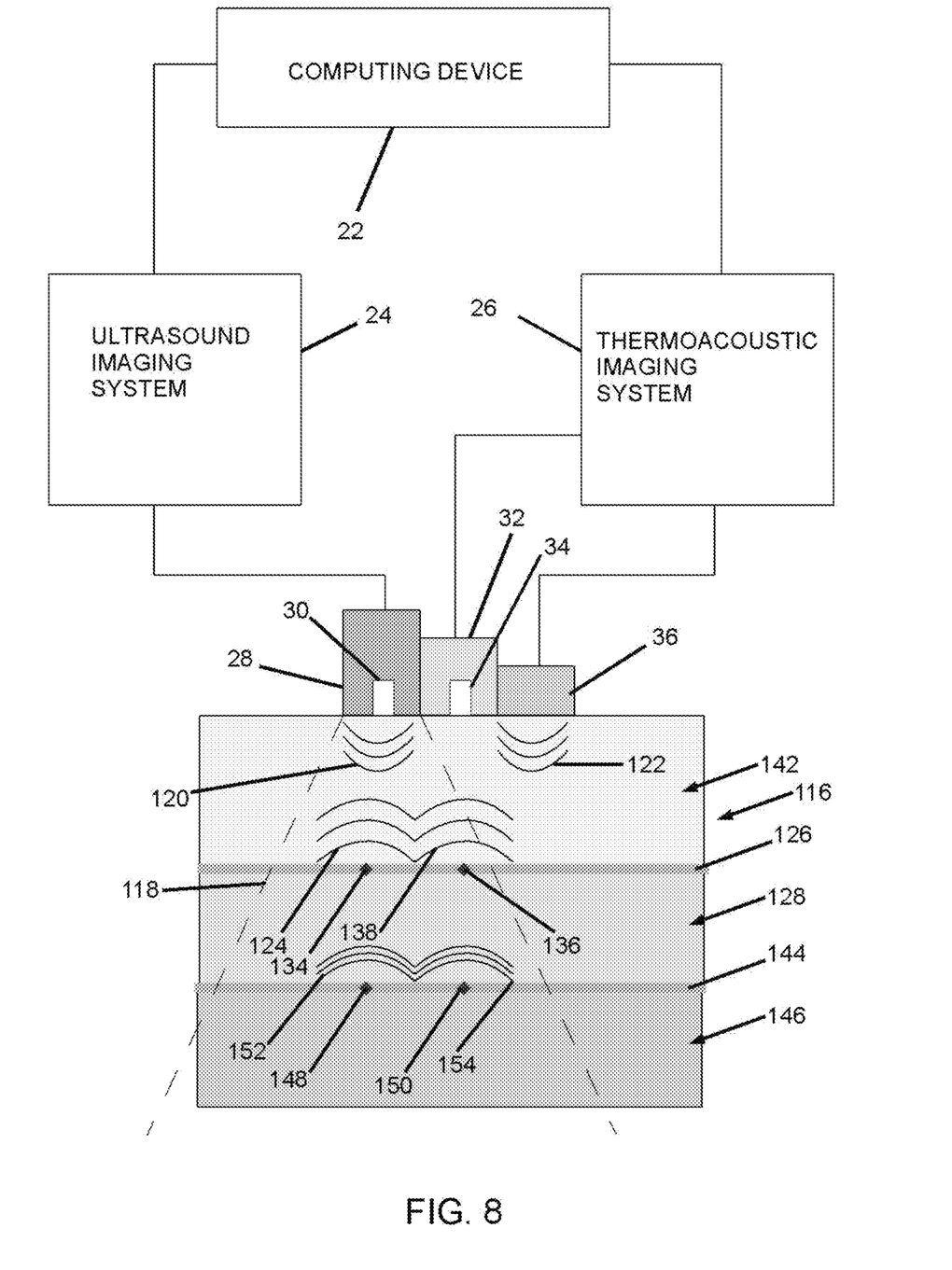
FIG. 8 is a schematic view of another embodiment of an imaging system.

Although in embodiments a single boundary, a single material of interest and a single reference are imaged, those skilled in the art will appreciate that alternatives are available. An example is shown in FIG. 8. In this embodiment, a user utilizes the computing device 22 to operate the ultrasound imaging system 24. The ultrasound imaging system 24 sends a signal to the one or more ultrasound transducer arrays 30, which sends sound waves into known reference 142 which is in the form of a pad made of a known material and is positioned within the region of interest 116. Within the region of interest 116, there is a first boundary 126 at first boundary locations 134 and 136, a first material of interest 128, a second material of interest 146, and a second boundary 144 at second boundary locations 148 and 150. The ultrasound transducer arrays 30 receive reflected sound waves to generate a B-mode image via the ultrasound imaging system 24. The extent of the B-mode image is conical in shape and is shown with B-mode image limits 118. The B-mode image gives the physical location of boundary 126, enabling the computing device 22 to correlate obtained data from the thermoacoustic transducer array 34 and RF emitter 36. Once position coordinates are known, the ultrasound imaging system 24 is turned off to eliminate potential interference with the thermoacoustic imaging system 26. The thermoacoustic imaging system then initiates the RF emitter 36 to send RF energy pulses 122 into reference 142. The RF energy pulses 122 are absorbed in the region of interest 116. The difference between RF energy absorbed in the reference 142 and the first material of interest 128 creates thermoacoustic multi-polar signals 124 and 138 emanating from boundary locations 134 and 136. In addition, the difference between RF energy absorbed in the first material of interest 128 and the second material of interest 146 creates thermoacoustic multi-polar signals 152 and 154 emanating from boundary locations 148 and 150. The known parameters of the reference 142 can then be used in conjunction with thermoacoustic data from the thermoacoustic multi-polar signals generated at boundary locations 134 and 136 to determine a parameter of the first material of interest 128. Additionally, properties or parameters of the first material of interest 128 can be used in conjunction with thermoacoustic data from the thermoacoustic multi-polar signals generated at boundary locations 148 and 150 to determine a parameter of the second material of interest 146.

Although in embodiments described above the one or more ultrasound transducer arrays are described as being disconnectable from the ultrasound imaging system and reconnectable to the thermoacoustic imaging system, those skilled in the art will appreciate that alternatives are available. For example, the one or more ultrasound transducer arrays may be connected to a hub which itself is connected to the ultrasound imaging system 24 and the thermoacoustic imaging system 26. In this embodiment, the hub may be controlled by the computing device 22 or by other input to switch operation between the ultrasound imaging system 24 and the thermoacoustic imaging system 26 and vice versa.

Although in embodiments described above the thermoacoustic data is described as being in the form of thermoacoustic multi-polar signals, those skilled in the art will appreciate that the thermoacoustic data may be in the form of other multipolar signals.

Although in embodiments described above a metric used to estimate the signal strength at the boundary is the difference between two or more peaks of a thermoacoustic multi-polar signal, those skilled in the art will appreciate that the metric may be a simple peak (maximum), a p-norm, area under the thermoacoustic multi-polar signal, etc.

As will be appreciated, embodiments of image processing described above can be performed on ultrasound and thermoacoustic images in real-time or off-line using images stored in memory.

Although the thermoacoustic imaging system 26 is described as comprising an RF applicator 36 configured to generate short pulses of RF electromagnetic radiation, those skilled in the art will appreciate that in other embodiments the thermoacoustic imaging system may comprise a visible light source or an infrared radiation source with a wavelength between 400 nm and 10 μm and a pulse duration between 10 picoseconds and 10 microseconds.

Although in embodiments described above the thermoacoustic imaging system 26 and the ultrasound imaging system 24 are described as using one or more ultrasound transducer arrays, those skilled in the art will appreciate that the alternatives are available. For example, a single transducer element, an ultrasound transducer array having a linear or curved one-dimensional array, or a two-dimensional ultrasound transducer array may be used.

Although in embodiments described above, thermoacoustic data is obtained of a single region of interest, those skilled in the art will appreciate that multiple regions of interest may be analyzed and combined.

Those skilled in the art will appreciate that the above-described ultrasound image data and thermoacoustic data may be one-dimensional, two-dimensional or three-dimensional. In embodiments, the ultrasound image data may be in a different dimension than the thermoacoustic data. For example, ultrasound image data may be two-dimensional and the thermoacoustic data may be one-dimensional. Further, different fields of view may be used.

In another embodiment, different types or models of transducer arrays may be used with the thermoacoustic and ultrasound imaging systems. In this embodiment, a transform may be used to map a thermoacoustic absorption data to the ultrasound image. In another embodiment, in the event that knowledge of transducer array geometry is not readily available, the thermoacoustic absorption data may be mapped to the ultrasound image using a phantom with reference points. In this embodiment, a transform may be used to map known phantom reference points from the thermoacoustic absorption data to the phantom reference points on the ultrasound image.

Although the ultrasound imaging system 24 is described as using B-mode ultrasound imaging techniques, other techniques may be used such as for example power Doppler images, continuous wave Doppler images, strain imaging, etc.

Although in embodiments described above thermoacoustic data is obtained of the region of interest, those skilled in the art will appreciate that thermoacoustic data may be obtained for an area larger than the region of interest.

Those skilled in the art will appreciate that in embodiments the computing device 22 may be programmed to adjust parameters of the RF applicator 36.

Those skilled in the art will appreciate that the above-described method may be performed on a phantom designed to mimic an area of interest. In this embodiment, the RF applicator may be adjusted to maximize the peak-to-peak amplitudes of the thermoacoustic multi-polar signals prior to imaging a material. Further, the method may be performed on numerous phantoms of various properties to mimic different materials.

Although embodiments have been described above with reference to the accompanying drawings, those of skill in the art will appreciate that variations and modifications may be made without departing from the scope thereof as defined by the appended claims.

What is claimed is:

1. A method for determining a material type of an object of interest, the method comprising:
    directing, using a radio frequency (RF) source, RF energy into a region of interest, the region of interest comprising the object of interest, a known reference and a boundary between the object of interest and the known reference;
    detecting, using an acoustic receiver, at least one thermoacoustic multi-polar signal generated in response to the RF energy;
    correlating, by one or more processors, the at least one thermoacoustic multi-polar signal to a transmitted power correction factor to generate a corrected thermoacoustic multi-polar signal; and
    determining, by the one or more processors, the material type of the object of interest as a function of the corrected thermoacoustic multi-polar signal and a transmitted power of the RF energy.

2. The method of claim 1, wherein the directing, using a radio frequency (RF) source, RF energy into a region of interest, comprises using a thermoacoustic imaging system to direct RF energy pulses into the region of interest.

3. The method of claim 2, wherein the detecting, using the acoustic receiver, at least one thermoacoustic multi-polar signal generated in response to the RF energy, comprises using at least one thermoacoustic transducer array or at least one ultrasound transducer array.

4. The method of claim 1, comprising determining the transmitted power correction factor determined based on an input power of the RF source and an attenuation coefficient of the known reference.

5. The method of claim 1, comprising determining the transmitted power correction factor based on an estimated thickness of the known reference and an attenuation coefficient of the known reference.

6. The method of claim 1, wherein each thermoacoustic multi-polar signal corresponds to a separate boundary location.

7. The method of claim 6, further comprising:
    directing, using an ultrasound system, sound waves into the region of interest;
    detecting, using an ultrasonic transducer of the ultrasound system, echoes generated in the region of interest in response to the sound waves;
    processing ultrasound data associated with the echoes to generate one or more or more ultrasound images; and
    using the one or more ultrasound images to locate the region of interest.

8. The method of claim 1, wherein determining the material type of the object of interest is further based on at least one physical characteristic of the object of interest.

9. The method of claim 8, wherein the at least one physical characteristic is at least one of color, transparency, odor, texture and material state.

10. The method of claim 1, wherein the object of interest is tissue within a human body and the known reference is lean tissue within the human body.

11. A system for determining a material type of an object of interest, the system comprising:
    a radio frequency (RF) source configured to direct RF energy toward the region of interest, wherein the region of interest comprises the object of interest, a known reference, and a boundary between the object of interest and the known reference;
    at least one thermoacoustic or ultrasonic transducer configured to receive a thermoacoustic multi-polar signal generated in response to the RF energy signal; and
    one or more processors configured to correlate the thermoacoustic multi-polar signal to a transmitted power correction factor to generate a corrected thermoacoustic multi-polar signal and to determine the material type of the object of interest as a function of the corrected thermoacoustic multi-polar signal and a transmitted power of the RF energy.

12. The system of claim 11, wherein the RF source is configured to direct RF energy pulses into the region of interest.

13. The system of claim 11, wherein the transmitted power correction factor is determined based on an input power of the RF source and an attenuation coefficient of the known reference.

14. The system of claim 11, wherein the transmitted power correction factor is determined based on an estimated thickness of the known reference and an attenuation coefficient of the known reference.

15. The system of claim 11, wherein each thermoacoustic multi-polar signal corresponds to a separate boundary location.

16. The system of claim 11, further comprising an ultrasound imaging system configured to direct sound waves into the region of interest and detect echoes generated in the region of interest in response to the sound waves and wherein the one or more processors are configured to process ultrasound data associated with the echoes to generate one or more or more ultrasound images and use the one or more ultrasound images to locate the region of interest.

17. The system of claim 11, wherein the one or more processors are configured to determine the material type of the object of interest further based on at least one physical characteristic of the object of interest.

18. The system of claim 17, wherein the at least one physical characteristic is at least one of color, transparency, odor, texture and material state.

19. The system of claim 11, wherein the known reference is one of a container and a pad.

20. A system for determining a material type of an object of interest, the system comprising:
    a thermoacoustic imaging system comprising a radio frequency (RF) applicator configured to emit RF energy pulses into the region of interest, the region of interest comprising an object of interest and a known reference separated by at least one boundary and an acoustic receiver configured to receive at least one thermoacoustic multi-polar signal induced in the region of interest in response to the RF energy pulses; and
    one or more processors configured to:
        correlate the at least one thermoacoustic multi-polar signal to a transmitted power correction factor to generate a corrected thermoacoustic multi-polar signal; and determine the material type of the object of interest as a function of the corrected thermoacoustic multipolar signal and a transmitted power of the RF energy pulses.

* * * * *